United States Patent [19]
Westlake, III et al.

[11] Patent Number: 5,398,559
[45] Date of Patent: Mar. 21, 1995

[54] SAMPLE PROBE WITH TEMPERATURE MONITORING AND/OR CONTROL

[75] Inventors: Theodore N. Westlake, III; Duane K. Wolcott, both of Baton Rouge, La.

[73] Assignee: The Dow Chemical Company, Midland, Mich.

[21] Appl. No.: 986,838

[22] Filed: Dec. 8, 1992

Related U.S. Application Data

[63] Continuation-in-part of Ser. No. 843,687, Feb. 28, 1992, Pat. No. 5,317,932.

[51] Int. Cl.⁶ .................... G01N 1/20; G01N 25/18
[52] U.S. Cl. ................... 73/863.81; 73/31.07; 73/64.56; 73/863.23; 73/25.03; 374/142; 374/147
[58] Field of Search ............ 73/864.73, 864.74, 866.5, 73/863.11, 863.12, 863.01–863.03, 863.41, 863.81, 863.86, 31.07, 61.55, 61.58, 61.59, 64.56, 64.55, 19.12, 29.05, 863.23, 25.03; 95/151, 158; 96/151, 219, 220; 210/321.74; 374/142, 147, 148

[56] References Cited

U.S. PATENT DOCUMENTS

| | | | |
|---|---|---|---|
| 3,830,106 | 8/1974 | Gardiner et al. | 73/863.81 |
| 4,569,228 | 2/1986 | Bellgardt et al. | 73/866.5 |
| 4,631,961 | 12/1986 | Yoke et al. | 73/866.5 |
| 4,832,034 | 5/1987 | Pizziconi et al. | 128/632 |
| 4,846,977 | 7/1989 | DeVellis et al. | 210/321.74 |
| 4,944,180 | 7/1990 | Tou et al. | 73/38 |
| 5,085,087 | 2/1992 | Franck et al. | 73/864.73 |
| 5,090,257 | 2/1992 | Bruce | 73/863.03 |
| 5,317,932 | 6/1994 | Westlake, III et al. | 73/864.73 |

OTHER PUBLICATIONS

Joseph Haggin, *Heated Membranes Give Improved Separation*, Chemical and Engineering News Apr. 27, 1992, p. 41.

Primary Examiner—Tom Noland

[57] ABSTRACT

An apparatus for use in determining the presence and/or concentration of one or more selected materials in a given stream or aggregation in a conduit or vessel, the apparatus comprising (a) a support member constructed from a thermally conductive material and having a first, internal end for inserting into the stream or aggregation when the apparatus is placed in service and a second end positioned externally of the conduit or vessel in use, wherein the support member defines a groove therein of which at least a portion extends into the stream or aggregation in use, (b) a conduit positioned and supported substantially wholly within at least that portion of the groove in the support member which extends into the stream or aggregation in use, and (c) a temperature monitoring device positioned within the support member, whereby the temperature of the conduit/stream or aggregation interface may be measured by thermal conduction from the supporting groove portion of the support member to the temperature monitoring device contained within the support member.

18 Claims, 3 Drawing Sheets

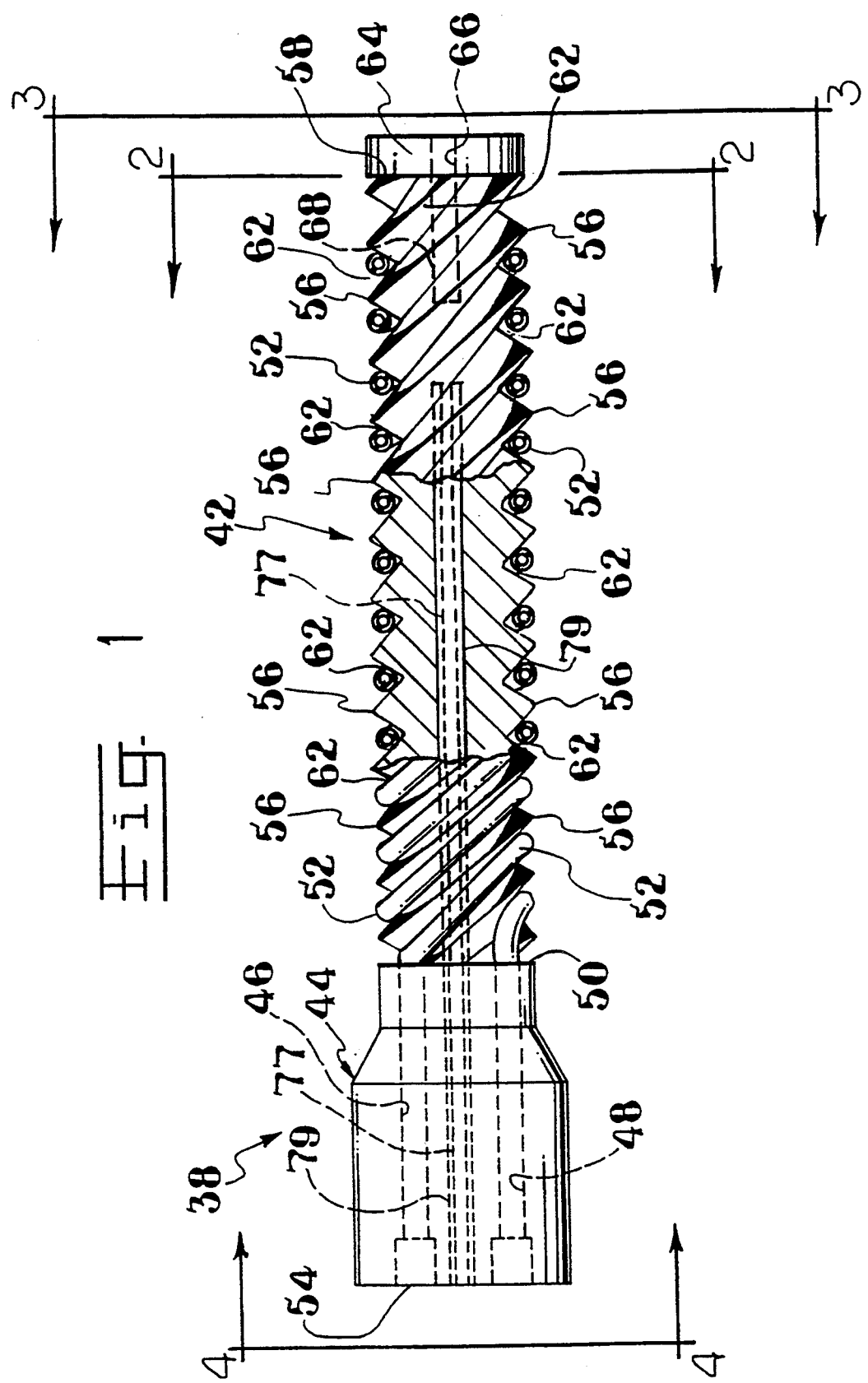

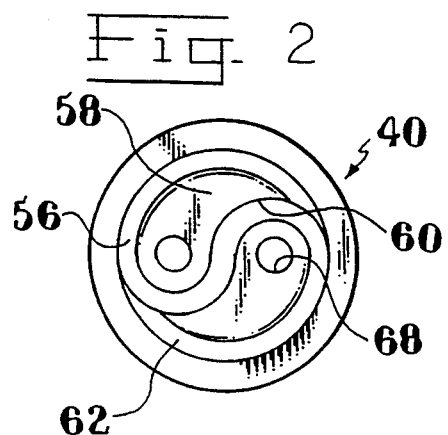
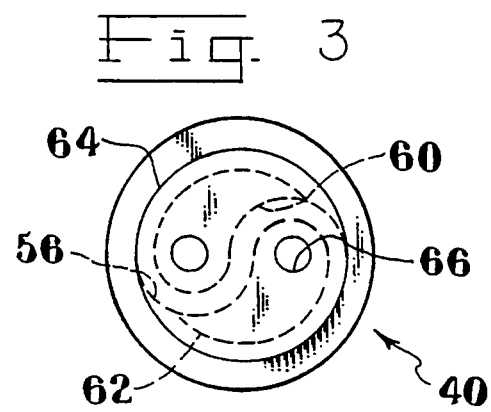
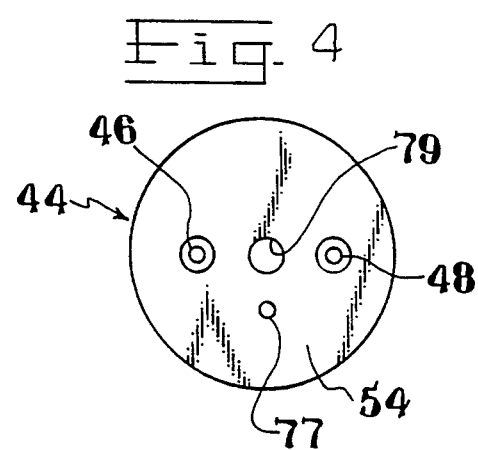

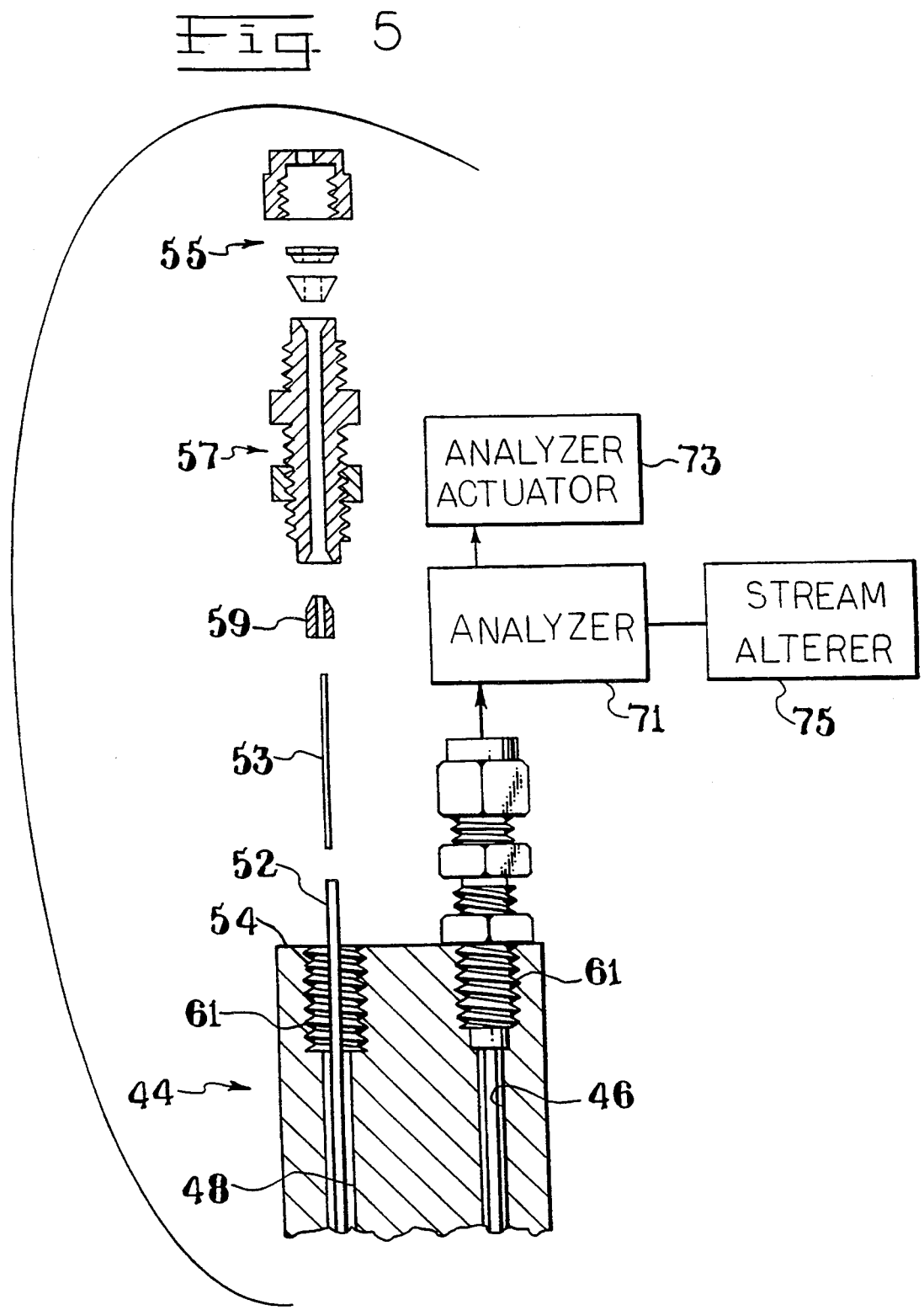

SAMPLE PROBE WITH TEMPERATURE MONITORING AND/OR CONTROL

CROSS REFERENCE TO RELATED APPLICATIONS

This application is a continuation-in-part of U.S. patent application Ser. No. 07/843,687, filed Feb. 28, 1992, now U.S. Pat. No. 5,317,932 such application being incorporated herein by reference.

BACKGROUND OF THE INVENTION

The present invention relates to devices for detecting, monitoring and/or measuring low-level concentrations of certain materials within a complex matrix stream or aggregation of flowable materials. In one of several, more particular aspects, the present invention relates to such devices which employ permeation membrane or diffusion membrane tubing in some fashion to collect and isolate these certain materials from within the stream or aggregation.

Tubular membranes have been suggested for use in this capacity in a number of analytical devices, and are particularly of interest for use in separating out those components of a complex stream or aggregation which might adversely affect a gas or liquid chromatograph or other analytical device if one attempted to analyze the stream or aggregation directly.

Because of the harsh sampling environment presented by many process streams and because of the fragility of the suitable tubular membranes, however, the previously known devices employing such tubular membranes have very largely been designed to operate on but a portion of the larger stream or aggregation.

The present inventors have previously developed and described a device in the referenced U.S. patent application Ser. No. 07/843,687 which is amenable to sampling from difficult process streams or aggregations by direct insertion. This feature represents a significant improvement over the previously-known devices. One formerly unresolved problem that the inventors have noted with a direct insertion device, though, relates to the influence of temperature on the membrane's permeation/transfer characteristics and accuracy.

In those devices wherein a small sample stream or aggregation is operated upon, it has been possible in the past to monitor and control the temperature of the sample stream or aggregation and to thus monitor and control, indirectly, the temperature at the tubular membrane/fluid interface. Obviously this is not going to be a very practical approach in the context of directly inserting a sample probe into most process streams of interest. And even in the context of a small sample stream (or slipstream) or aggregation, thermal conditioning of the entire sample stream or aggregation can be energy-intensive and troublesome, for example in causing degassing or precipitation of other soluble species in the stream or aggregation.

One device is reported in the literature for effecting a separation of a high-boiling organic solute (e.g., phenol, 4-hydroxydecanoic acid lactone) from a dilute aqueous solution of the solute via a heated tubular membrane instead of by thermal conditioning of the aqueous solution, see Haggin, "Heated Membranes Give Improved Separation", Chemical and Engineering News, Apr. 27, 1992, page 41. In this device, the membrane is internally reinforced with a woven wire mesh that can be heated and which enhances the desired separation, whereas heating the aqueous solution was found in the case of the phenol/water system to increase organic flux density but to reduce separation of the phenol from water.

SUMMARY OF THE INVENTION

In considering the above-mentioned problems and the shortcomings of the internally-reinforced membrane just described, the inventors have conceived of an improved apparatus for use in determining the presence and/or concentration of one or more selected materials in a given stream or aggregation of flowable materials in a conduit or vessel, the apparatus comprising (a) a support member constructed from a thermally conductive material and having a first, internal end for inserting into the stream or aggregation when the apparatus is placed in service and a second end positioned externally of the conduit or vessel in use, wherein the support member defines a groove therein of which at least a portion extends into the stream or aggregation in use, (b) a conduit positioned and supported substantially wholly (and preferably wholly) within at least that portion of the groove in the support member which extends into the stream or aggregation in use, and (c) a temperature monitoring device (e.g., a thermocouple or known resistive temperature device (RTD)) positioned within the support member, whereby the temperature of the conduit/stream or aggregation interface may be measured by thermal conduction from the supporting groove portion of the support member to the temperature monitoring device contained within the support member. In this manner, variations or differences in temperature may be taken into account in interpreting analytical data from an associated analytical device.

In a variation on this embodiment, one or more heaters (for example, cartridge heaters) are placed within the thermally conductive support member and, through association with one or more of the above-mentioned temperature monitoring devices, are controlled to provide different temperatures at the conduit/stream or aggregation interface (and thus different transport characteristics). "Conduit", as used in describing an element of the present invention above and elsewhere herein, is intended to embrace permeation membrane and diffusion membrane tubing.

BRIEF DESCRIPTION OF THE DRAWINGS

FIG. 1 substantially reproduces FIG. 5 of U.S. Ser. No. 07/843,687 (with certain alterations described more particularly below) in showing a side view in partial cross-section of a preferred embodiment of the apparatus of the present invention, and for clarity employs the same reference numbers as used in conjunction with FIG. 5 of U.S. Ser. No. 07/843,687 (which shall hereafter be referred to as the '687 application).

FIG. 2 substantially reproduces FIG. 6 of the '687 application, and provides a sectional view of the embodiment of FIG. 1 taken along line 2—2.

FIG. 3 substantially reproduces FIG. 7 of the '687 application, and provides an end view of the apparatus of FIG. 1 taken from the perspective of line 3—3.

FIG. 4 is taken from the opposite end of the apparatus from that shown in FIG. 3, and more particularly shows the alterations made by the present invention and referenced above.

FIG. 5 substantially reproduces FIG. 10 of the '687 application in showing a preferred manner of joining a source of a receiving fluid, the apparatus of FIGS. 1–4 and an analyzer in fluid communication, the alterations shown in FIGS. 1 and 4 having been omitted however from this Figure for ease of understanding.

DETAILED DESCRIPTION OF A PREFERRED EMBODIMENT OF THE INVENTION.

A preferred embodiment of the improved apparatus of the present invention will be based on the apparatus shown in FIGS. 5–7 of U.S. Ser. No. 07/843,687 and described in conjunction therewith. FIGS. 5–7 of the '687 application are substantially reproduced herein as FIGS. 1–3, except that the apparatus of FIGS. 5–7 has of course been modified in FIGS. 1–3 to accommodate the improved features provided by the present invention.

The basic apparatus of FIGS. 1–3 is comprehensively described in the '687 application. Briefly, however, a preferred embodiment 38 comprises a thermally-conductive support member 40 having a double-lead flight threaded portion 42 and an unthreaded portion 44. Two channels 46 and 48 are defined longitudinally through the unthreaded portion 44, and emerge at a shoulder 50 of the unthreaded portion 44 in position to receive from or transmit to a helical flight of the adjacent threaded portion 42 a tubular membrane 52 supported therein. Short, curving transition channels (not shown) may preferably be provided in the surface of the unthreaded portion 44 adjacent the shoulder 50 for easing the transition of the membrane 52 between the channels 46 and 48 and the flights of the threaded portion 42. Preferably capillary membrane ends placed in these channels 46 and 48 are adapted to be joined in fluid communication with a source (not shown) of a receiving fluid and with an analytical device such as a gas or liquid chromatograph or the like, respectively.

The presently preferred construction for joining the membrane 52 in communication with a source of a receiving fluid, and in turn with a gas or liquid chromatograph or other associated analytical device for determining the presence and/or concentration of one or more selected materials in a given stream or aggregation of flowable materials in a conduit or vessel into which the embodiment 38 is inserted (through permeation or diffusion transport into the membrane 52 from the stream or aggregation of a selected material and communication with the receiving fluid to the analytical device), is shown in FIG. 5. In this preferred construction, one end of a length of membranes support tubing 53 is inserted into and holds open the central lumens of the membrane tubing 52. This membrane support tubing 53 can be made of, for example, stainless steel or a fused silica glass.

Membrane support tubing 53 is in turn securely joined via a two ferrule compression-type fitting 55 to a conventional tubing lead (not shown, and comprised, e.g., of stainless steel or nickel) to the gas or liquid chromatograph or other analytical means 71. A compression-type tube-to-tube bulkhead fitting 57 ties the assembly 55 and a membrane sealing ferrule 59 into an integrated whole, with the fitting 57 being joined to the support member 40 by the threaded engagement of fitting 57 with a threaded portion 61 of a channel 46 or 48 in the unthreaded portion 44 of support member 40.

The membrane tubing 52 associated in use with the support member 40 thus enters the unthreaded portion 44 through channel 46 from a second end 54 of the member 40 and from a source of the receiving fluid to be employed in membrane 52.

Returning now to FIGS. 1–3, the membrane 52 is then wrapped around the support member 40 through alternating flights 56 (FIG. 1) toward a first end 58 of member 40, with the membrane 52 being positioned and supported substantially wholly (and preferably wholly) within the flights 56. At the first end 58 of the support member 40, and as best shown in FIG. 2, the membrane 52 then travels through an S-shaped channel 60 in the first end 58 of the support member 40 which joins the alternating helical flights 62 in communication with the flights 56. The membrane 52 in traversing flights 62 thus is wrapped around member 40 through those alternating flights which had been "skipped" in going from the second end 54 of the member 40 to the first end 58 of member 40.

The membrane 52 returns to and is received by the channel 48 in the unthreaded portion 44 of the support member 40. The receiving fluid and any selected materials collected by the membrane 52 from with a stream or aggregation of flowable materials in a process vessel and carried by the receiving fluid are communicated through channel 48 and by the arrangement depicted in FIG. 5 to an associated analytical means 71 as described previously, the analytical means 71 comprising for example a gas chromatograph/mass spectrometer combination or a liquid chromatograph.

A protective cap 64 is placed over the S-shaped channel 60 in the first end 58 of the support member 40, and is conventionally joined to the support member 40 as through bolts or screws placed through holes 66 in the cap 64 and corresponding holes 68 in the first end 58 of support member 40. The cap 64 retains the membrane 52 within the S-shaped channel 60, and may be used as a spacer to keep the membrane 52 from being damaged by being inserted too far into a process pipe and, for example, encountering fouling or the like on an inside wall of the pipe.

In the apparatus 38, and as reflected in the '687 application, the flights 56 and 62 may be seen as first and second connecting "grooves". "Groove" as used herein and in the claims which follow thus embraces a threaded flight on a given support member, but is not limited thereto. What is intended for purposes of the present invention and disclosure is that those portions of a membrane or conduit which are immersed in and exposed to potentially damaging or distorting environments should be protected from those environments, by being supported within a recessed portion of the body of a support member.

A continuous groove in the form of threads on a support member is to be preferred over a groove proceeding more directly from the first end to the second end of the device, and the double-lead flight threaded construction shown in the drawings and described above is to be preferred over a single flight threaded construction. It will in each of these devices additionally be preferred that the groove carrying the membrane/conduit (and obviously the membrane carried in the groove) extend from the first, internal end of the support member in such a device to an interior wall of the process pipe, reactor or other vessel in which the apparatus is used, or where the stream in question does not substantially fill a pipe or vessel to such interior wall, at least span as much of the matrix stream to be monitored as possible. In this manner a large contact area is established between the membrane and the stream or aggregation of flowable materials to be monitored over which mass transport cain occur.

With reference to the most preferred embodiment 38, the interface between the threaded and unthreaded portions 42 and 44 thereof will thus preferably correspond closely (in most cases) to the interior wall of a vessel or pipe in which the apparatus is employed.

The circulation of a receiving fluid and/or the analysis of the receiving fluid from the membrane of a device of the present invention may be manually initiated, or one or both may preferably be initiated as shown in FIG. 5, by some conventionally-known remote automated means 73 for accomplishing this function so that sampling and analysis of a process stream may be more conveniently done. Suitable apparatus are described, for example, in *Automated Stream Analysis For Process Control*, Vol. 1 (Academic Press, Manka ed., 1982) and Nichols, *On-Line Process Analyzers* (John Wiley & Sons, 1988).

It will be preferred in many applications, also, that the means 71 for analyzing the receiving fluid from the membrane be coupled as shown in FIG. 5 to some sort of process control, for example, to any conventionally-known means 75 for altering the course and/or composition of the stream being monitored responsive, for example, to the presence in the stream of a given concentration of one or more selected materials.

The improvements offered by the present invention to the above-described apparatus of the '687 application lie in the provision of temperature monitoring means within, for example, the thermally conductive support member 40 of the embodiment 38 shown in FIGS. 1–5. Where temperature monitoring only is desired, a single well 77 can be drilled in the support member 40 from the second, external end 54 of the support member 40 toward the first, internal end 58 of the support member 40. Preferably the well 77 extends substantially over the entire length of the support member 40. Any suitable temperature measuring device can be placed in the well, 77 for example a thermocouple or other known resistive temperature device (RTD). Where some form of temperature control is desired in addition to temperature monitoring, one or more wells 79 of a like nature are preferably drilled in the support member 40, and cartridge heaters or the like are placed therein which are RTD-controlled.

The provision of a temperature monitoring device in the support member of an apparatus of the present invention permits for temperature compensation in the analysis of data from an associated analytical device, e.g., a gas chromatograph, while the heater permits the temperature of the conduit/stream or aggregation interface to be efficiently controlled for better separations even in the midst of a much larger process stream or aggregation of flowable materials. The presence of the heater also permits a periodic bake-off cycle to drive off less volatile materials which might coat the conduit over time.

Applications of the present inventive apparatus include its use in much larger process streams and in reactor vessels, in monitoring the outfall from a process for permitted materials, and in bench-scale analytical work. A good example of the last category is the replacement of the sample sparger of a conventional purge and trap device by the apparatus of the present invention (or for that matter by the apparatus of U.S. Ser. No. 07/843,687). By heating the support member and membrane carried thereon to a suitable temperature, volatile organic materials can be quantitatively removed, for example, from a wastewater or outfall sample and analyzed on an associated gas chromatograph in conventional purge and trap operation.

While preferred embodiments of the apparatus have been described herein, those skilled in the art will recognize that numerous changes and modifications may be made to these embodiments which are nevertheless within the scope and spirit of the present invention, and which are accordingly intended to be embraced by the claims following hereafter.

What is claimed is:

1. An apparatus for use in determining the presence and/or concentration of one or more selected materials in a given stream or aggregation of flowable materials in a conduit or vessel, the apparatus comprising:
   (a) a support member constructed from a thermally conductive material and having a first, internal end for inserting into the stream or aggregation when the apparatus is placed in service and a second end positioned externally of the conduit or vessel in use, wherein the support member defines a groove therein of which at least a portion extends into the stream or aggregation in use;
   (b) a conduit positioned and supported substantially wholly within at least that portion of the groove in the support member which extends into the stream or aggregation in use; and
   (c) a temperature monitoring device positioned within the support member, whereby the temperature of the conduit/stream or aggregation interface may be measured by thermal conduction from the supporting groove portion of the support member to the temperature monitoring device contained within the support member.

2. An apparatus as defined in claim 1, further comprising one or more heaters placed within the thermally conductive support member.

3. An apparatus as defined in claim 2, wherein the conduit is positioned and supported wholly within the groove.

4. An apparatus as defined in claim 2, wherein the groove extends continuously from an interior wall of the conduit or vessel to the first internal end of the support member, and wherein the support member defines a second groove therein in communication with the first groove which extends continuously from the first internal end of the support member to the interior wall.

5. An apparatus as defined in claim 4, wherein the first and second grooves of the support member consist of alternating helical flights of a double lead threaded support member, and wherein the conduit is positioned in troughs of such flights and is flanked by walls defining the flights of the support member, crests of walls on either side of the conduit in a respective flight extending above the trough and laterally from the support member to a greater extent than the conduit.

6. An apparatus as defined in claim 5, wherein the conduit is a tubular membrane, and the apparatus further comprises means for communicating the one or more materials collected from the stream or aggregation of flowable materials by the tubular membrane to an analytical device.

7. An apparatus as defined in claim 6, further comprising a protective spacer attached to the support member at the first, internal end of the support member.

8. An apparatus as defined in claim 1, wherein the conduit is positioned and supported wholly within the groove.

9. An apparatus as defined in claim 1, wherein the groove extends continuously from an interior wall of the conduit or vessel to the first internal end of the support member, and wherein the support member defines a second groove therein in communication with the first groove which extends continuously from the first internal end of the support member to the interior wall.

10. An apparatus as defined in claim 9, wherein the first and second grooves of the support member consist of alternating helical flights of a double lead threaded support member, and wherein the conduit is positioned in troughs of such flights and is flanked by walls defining the flights of the support member, crests of walls on either side of the conduit in a respective flight extending above the trough and laterally from the support member to a greater extent than the conduit.

11. An apparatus as defined in claim 10, wherein the conduit is a tubular membrane, and the apparatus further comprises means for communicating the one or more materials collected from the stream or aggregation of flowable materials by the tubular membrane to an analytical device.

12. An apparatus as defined in claim 11, further comprising a protective spacer attached to the support member at the first, internal end of the support member.

13. An apparatus for use in determining the presence and/or concentration of one or more selected materials in a given stream or aggregation of flowable materials within a conduit or vessel, comprising:
(a) a support member constructed from a thermally conductive material and having a first, internal end for inserting into the stream or aggregation when the apparatus is placed in service and a second end positioned externally of the conduit or vessel in use, wherein the support member defines a groove therein of which at least a portion extends into the stream or aggregation in use;
(b) a conduit positioned and supported substantially wholly within at least that portion of the groove in the support member which extends into the stream or aggregation in use;
(c) a temperature monitoring device positioned within the support member, whereby the temperature of the conduit/stream or aggregation interface may be measured by thermal conduction from the supporting groove portion of the support member to the temperature monitoring device contained within the support member; and
(d) analytical means, associated and in communication with the conduit in use, for determining the presence and/or concentration of the one or more selected materials.

14. An apparatus as defined in claim 13, further comprising one or more heaters placed within the thermally conductive support member.

15. An apparatus as defined in claim 14, further comprising means for programmably actuating the analyzing means.

16. An apparatus as defined in claim 14, further comprising means for altering the course and/or composition of the stream or aggregation of materials responsive to the presence of a given concentration of the one or more selected materials in said stream or aggregation.

17. An apparatus as defined in claim 13, further comprising means for programmably actuating the analyzing means.

18. An apparatus as defined in claim 13, further comprising means for altering the course and/or composition of the stream or aggregation of materials responsive to the presence of a given concentration of the one or more selected materials in said stream or aggregation.

* * * * *